(12) United States Patent
Sanders, Jr. et al.

(10) Patent No.: US 7,875,758 B2
(45) Date of Patent: Jan. 25, 2011

(54) SYSTEMS AND METHODS FOR THE SEPARATION OF PROPYLENE AND PROPANE

(75) Inventors: Edgar S. Sanders, Jr., Newark, DE (US); Frederic P. C. M. Noel, Saint Jean de la Ruelle (FR)

(73) Assignee: L'Air Liquide, Societe Anonyme pour l'Etude Et l'Exploitation des Procedes George Claude, Paris (FR)

( * ) Notice: Subject to any disclaimer, the term of this patent is extended or adjusted under 35 U.S.C. 154(b) by 345 days.

(21) Appl. No.: 11/968,507

(22) Filed: Jan. 2, 2008

(65) Prior Publication Data

US 2008/0167512 A1 Jul. 10, 2008

Related U.S. Application Data

(60) Provisional application No. 60/884,013, filed on Jan. 8, 2007.

(51) Int. Cl.
C07C 7/144 (2006.01)

(52) U.S. Cl. .................................. 585/818; 210/649

(58) Field of Classification Search .................. None
See application file for complete search history.

(56) References Cited

U.S. PATENT DOCUMENTS

| | | | |
|---|---|---|---|
| 3,758,603 A | 9/1973 | Steigelmann et al. | |
| 3,864,418 A | 2/1975 | Hughes et al. | |
| 4,060,566 A | 11/1977 | Yahnke | |
| 4,374,657 A | 2/1983 | Schendel et al. | |
| 4,444,571 A | 4/1984 | Matson | |
| 4,614,524 A | 9/1986 | Kraus | |
| 4,857,078 A | 8/1989 | Watler | |
| 4,952,751 A | 8/1990 | Blume et al. | |
| 4,978,430 A | 12/1990 | Nakagawa et al. | |
| 5,057,641 A | 10/1991 | Valus et al. | |
| 5,273,572 A | 12/1993 | Baker et al. | |
| 5,326,385 A | 7/1994 | Rajani et al. | |
| 5,679,133 A | 10/1997 | Moll et al. | |
| 6,187,196 B1 | 2/2001 | Way et al. | |
| 6,187,987 B1 | 2/2001 | Chin et al. | |
| 6,517,611 B1 | 2/2003 | Kuznicki et al. | |
| 6,693,018 B2 | 2/2004 | Kim et al. | |
| 6,986,802 B2 | 1/2006 | Colling et al. | |
| 7,018,445 B2 | 3/2006 | Simmons et al. | |
| 7,025,804 B2 | 4/2006 | Simmons et al. | |
| 7,070,694 B2 | 7/2006 | Colling et al. | |
| 2004/0000513 A1 | 1/2004 | Colling et al. | |
| 2004/0004040 A1* | 1/2004 | Colling et al. | .............. 210/641 |

(Continued)

OTHER PUBLICATIONS

Ilinich, O.M. and Zamaraev, K.I., "Separation of ethylene and ethane over polyphenyleneoxides membranes: transient increase of selectivity," Journal of Membrane Science, vol. 82, 1993, pp. 149-155.

(Continued)

Primary Examiner—Tam M Nguyen
(74) Attorney, Agent, or Firm—Christoopher J. Cronin (57) ABSTRACT

Embodiments of the present invention generally disclose membrane-based systems and methods for the separation of propylene and propane that overcome certain issues associated with prior art devices and take advantage of a temperature drop across the associated separation membrane.

15 Claims, 6 Drawing Sheets

U.S. PATENT DOCUMENTS

2004/0147796 A1* 7/2004 Roman et al. ............... 585/820
2004/0182786 A1 9/2004 Colling et al.

OTHER PUBLICATIONS

Ilinithc, O.M. and Lapkin, A.A. and Zamaraev, K.I., "Propylene in polyphenylene oxides membranes: unusual permeability vs. pressure behavior," Journal of Membrane Science, vol. 99, 1995, pp. 287-290.

Ilinitch, O.M. and Semin, G.L., and Chertova, M.V. and Zamaraev, K.I., "Novel Polymeric Membranes for Separation of Hydrocarbons," Journal of Membrane Science, vol. 66, 1992, pp. 1-8.

Krol, J.J. and Boerrigter, M. and Koops, G.H., Polyimide hollow fiber gas separation membranes: preparation and the suppression of plasticization in propane/propylene environments, Journal of Membrane Science, vol. 184, 2001, pp. 275-286.

Lee, Kwang-Rae and Hwang, Sun-Tak, "Separation of propylene and propane by polyimide hollow-fiber membrane module," Journal of Membrane Science, vol. 73, 1992, pp. 37-45.

Pinnau, Ingo and Toy, Lora G., "Solid polymer electrolyte composite membranes for olefin/paraffin separation," Journal of Membrane Science, vol. 184, 2001, pp. 39-48.

Tanaka, K., et al., "Premeation and separation properties of polyimide membranes to olefins and paraffins," Journal of Membrane Science, vol. 121, 1996, pp. 197-207.

Avgidou, M.S. and Kaldis, S.P. and Sakellaropoulos, G.P., "Membrane cascade schemes for the separation of LPG olefins and paraffins," Journal of Membrane Science, 2004, 17 pgs.

International Search Report for PCT/IB2008/050011.

* cited by examiner

| P (feed) (psia/KPa) | T (feed) (°C) | V/L Feed | T (Residue and permeate) (°C) | V/L Residue |
|---|---|---|---|---|
| 314/2.16e+3 | 90 | 1.00 | 77 | 1.00 |
| 400/2.76e+3 | 90 | 1.00 | 77 | 0.912 |
| 500/3.45e+3 | 90 | 1.00 | 87 | 0.330 |
| 600/4.14e+3 | 90 | 0.992 | 77 | 0 |
| 700/4.83e+3 | 90 | 0 | 20 | 0 |

SYSTEMS AND METHODS FOR THE SEPARATION OF PROPYLENE AND PROPANE

RELATED APPLICATIONS

This application claims priority to U.S. provisional application 60/884,013, filed Jan. 8, 2007, titled "Improved Systems and Methods for the Separation of Propylene and Propane", the contents of which are hereby incorporated by reference as if they were presented in the entirety herein.

BACKGROUND OF THE INVENTION

Olefins, particularly ethylene and propylene, are important chemical feedstocks. Typically they are found in nature or are produced as primary products or byproducts in mixtures that contain saturated hydrocarbons and other components. Before the raw olefins can be used, they usually must be purified from these mixtures. Numerous difficulties have been experienced in this type of separation. Due to their similar relative volatilities, energy-intensive, capital-intensive, multi-trayed distillation columns typically have been used for the purification of light olefins.

Figure 1:
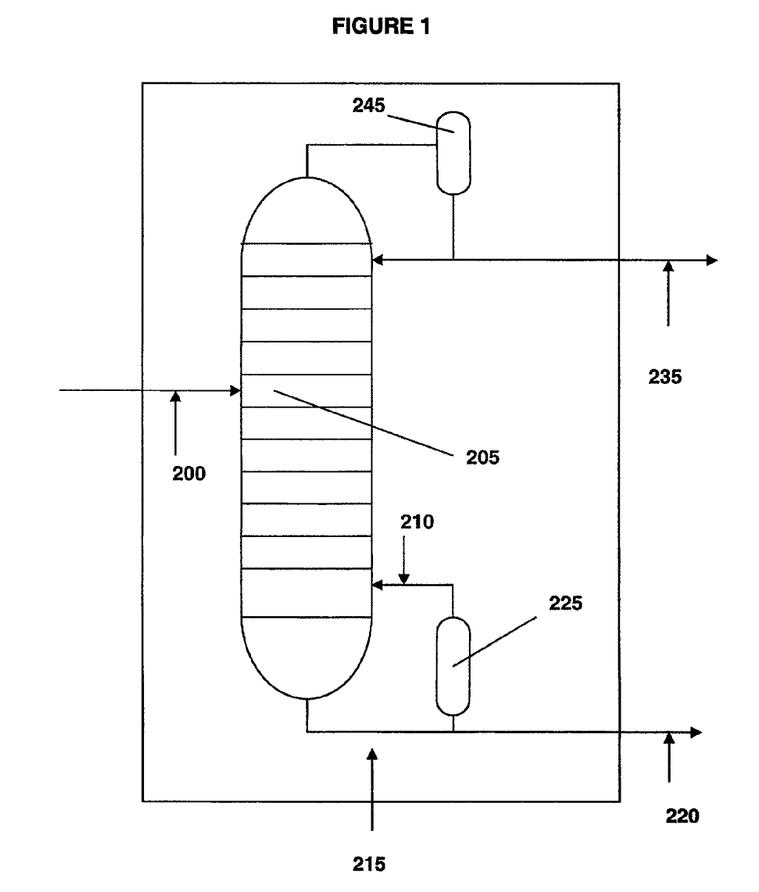
FIG. 1 is an illustration of a flow diagram showing a prior art distillation column for the separation of propylene and propane.

An example of a prior art distillation column for the separation of propylene and propane is illustrated in FIG. 1. In an exemplary method of operation, a raw feedstock of Refinery Grade Propylene (RGP) comprising 70% propylene and 30% propane is introduced to distillation column 205 along feed pipe or pipes 200. Distillation column 205 generally comprises multiple trays, or levels. In an embodiment, distillation column 205 comprises 135 trays. Operation of a distillation column is primarily determined by a combination of the number of trays and the reflux ratio. In general, the more trays in a distillation column, the greater the separation at a constant reflux ratio, but also the greater the capital cost. Conversely, fewer trays can be used if reflux is increased, but operating cost is increased. In the distillation column, the lighter components tend to rise and the heavier components tend to sink. Accordingly, a propylene product stream is capable of being extracted along piping 235. In an embodiment, the propylene is extracted as Commercial Grade Propylene (CGP nominally 93% propylene).

A second stream comprising propylene and other lighter components can be extracted from column 205, re-condensed and injected back into column 205 along piping 210. A propane product typically greater than 95% propane, can be extracted about piping 215. The extracted products can be passed through heat exchangers 245 and/or 225 to aid in the control or change of various streams within the process.

Column 205 is merely one example of a propylene and propane distillation column. One of ordinary skill in the art would readily understand that many variations are possible.

Typical results from a single distillation column, with a 70% propylene feed, produces a propylene product of 93% purity and a propane product of 95%. Accordingly, an improved system would produce results at least as good as a typical prior art distillation column.

The art field has desired to use a membrane-based system. U.S. Pat. No. 3,758,603 and U.S. Pat. No. 3,864,418 in the names of Robert D. Hughes and Edward F. Steigelmann describe membranes used in conjunction with metal complexing techniques to facilitate the separation of ethylene from ethane and methane. Similar metal complex and membrane hybrid processes, called facilitated transport membranes, have been described in U.S. Pat. No. 4,060,566 in the name of Robert L. Yahnke and in U.S. Pat. No. 4,614,524 in the name of Menahem A. Kraus.

Further membranes have been considered for the separation of olefins from paraffins as an alternative to distillation. However, the separation is difficult largely because of the similar molecular sizes and condensability of the components desired to be separated. The membrane must operate in a hydrocarbon environment under conditions of high pressure and temperature, often resulting in plasticization and can cause loss of selectivity and/or permeation rate. Such harsh conditions tend to adversely affect the durability and stability of separation performance of many membrane materials. A membrane system with sufficiently high olefin/paraffin selectivity, high productivity, and sufficient durability in long-term contact with hydrocarbon streams under high pressure and temperature is highly desired.

The art is replete with processes said to fabricate membranes possessing both high selectivity and high fluxes. Without sufficiently high fluxes the required membrane areas required would be so large as to make the technique uneconomical. It is now well known that numerous polymers are much more permeable to polar gases (examples include $H_2O$, $CO_2$, $H_2S$, and $SO_2$) than to nonpolar gases ($N_2$, $O_2$, and $CH_4$), and that gases of small molecular size (He, $H_2$) permeate more readily through polymers than large molecules ($CH_4$, $C_2H_6$).

However, even considering these difficulties, utilization of membrane separation has taken an important place in chemical technology for use in a broad range application. Gas separation has become a major industrial application of membrane technology in the last 15 years. Membrane based technology for the production of nitrogen from air, removal of carbon dioxide from natural gas, and purification of hydrogen now occupy significant shares of the markets for these processes.

Membrane materials and systems for separating olefinic hydrocarbons from a mixture of olefinic and saturated hydrocarbons have been reported, but none can be easily or economically fabricated into membranes that offer the unique combination of high selectivity and durability under industrial process conditions to provide economic viability.

For example, several inorganic and polymer/inorganic membrane materials with good propylene/propane selectivity have been studied. However, the art filed has found it difficult to fabricate these membranes into practical industrial membranes. Likewise, liquid facilitated-transport membranes have been demonstrated to have attractive separation performance in the lab, but have been difficult to scale up, and have exhibited declining performance in environments typical of an industrial propylene/propane stream.

Solid polymer-electrolyte facilitated-transport membranes have shown to be capable of fabrication into more stable thin film membranes for ethylene/ethane separation. See Ingo Pinnau and L. G. Toy, Solid polymer electrolyte composite membranes for olefin/paraffin separation, J. Membrane Science, 184 (2001) 39-48. However, these membranes are severely limited by their chemical stability in the olefin/paraffin industrial environment.

Carbon hollow-fiber membranes have shown promise in laboratory tests ("Propylene/Propane Separation", Product Information from Carbon Membranes, Ltd., Israel), but are vulnerable to degradation caused by condensable organics or water present in industrial streams. Moreover, carbon membranes are brittle and difficult to form into membrane modules of commercial relevance.

Membranes based on rubbery polymers typically have olefin/paraffin selectivity too low for an economically useful separation. For example, Tanaka et al. report that the single-gas propylene/propane selectivity is only 1.7 for a polybutadiene membrane at 50° C. (K. Tanaka, A. Taguchi, Jianquiang Hao, H. Kita, K. Okamoto, J. Membrane Science 121 (1996) 197-207) and Ito reports a propylene/propane selectivity only slightly over 1.0 in silicone rubber at 40° C. (Akira Ito and Sun-Tak Hwang, J. Applied Polymer Science, 38 (1989) 483-490).

Membranes based on glassy polymers have the potential for providing usefully high olefin/paraffin selectivity because of the preferential diffusivity of the olefin, which has smaller molecular size than the paraffin.

Membrane films of poly(2,6-dimethyl-1,4-phenylene oxide) exhibited pure gas propylene/propane selectivity of 9.1 (Ito and Hwang, Ibid.) Higher selectivity has been reported by Ilinitch et al. (J. Membrane Science 98 (1995) 287-290, J. Membrane Science 82 (1993) 149-155, and J. Membrane Science 66 (1992) 1-8). However, the membrane exhibited plasticization, most likely due to the presence of hydrocarbons.

Polyimide membranes have been studied extensively for the separation of gases. Lee et al. (Kwang-Rae Lee and Sun-Tak Hwang, Separation of propylene and propane by polyimide hollow-fiber membrane module, J. Membrane Science 73 (1992) 37-45). The article discloses a hollow fiber membrane of a polyimide that exhibits a mixed-gas propylene/propane selectivity in the range of 5-8 with low feed pressure (2-4 bar).

Krol et al. (J. J. Krol, M. Boerrigter, G. H. Koops, Polyimide hollow fiber gas separation membranes: preparation and the suppression of plasticization in propane/propylene environments, J. Membrane Science. 184 (2001) 275-286) report a hollow fiber membrane of a polyimide composed of biphenyltetracarboxylic dianhydride and diaminophenylindane which exhibited a pure-gas propylene/propane selectivity of 12. However, this membrane was plasticized at even low pressures.

Many of these prior art membrane-based techniques of propane/propylene separation utilize a pervaporation mode (liquid feed, gaseous permeate) or gas separation mode (gaseous feed, gaseous permeate). In the pervaporation mode of operation, the liquid feed is "evaporated" to the permeate stream. The latent heat of vaporization is large and a large temperature decrease accompanies the separation. Pervaporation based separation has similarities to propane refrigeration. The high pressure feed permeates the membrane to low pressure. This process is similar to the expansion of propane across an expansion valve in s propylene refrigeration system.

A convenient mathematical method of describing pervaporation is to divide the separation into two steps. The first is evaporation of the feed liquid to form a hypothetical saturated vapor phase on the feed side of the membrane. The second is permeation of this vapor through the membrane to the low pressure permeate side of the membrane. Although no evaporation actually takes place on the feed side of the membrane during pervaporation, this approach is mathematically simple and is thermodynamically equivalent to the physical process.

In pervaporation, transmembrane permeation is typically induced by maintaining the pressure on the permeate side lower than the vapor pressure of the feed liquid. The permeate side pressure can be reduced, for example, by drawing a vacuum on the permeate side of the membrane, by sweeping the permeate side to continuously remove permeating vapor, or by cooling the permeate vapor stream to induce condensation. The feed may also be heated to raise the vapor pressure on the feed side or to at least partially compensate for the temperature drop on permeation.

Certain issues accompany the use of pervaporation, namely, and typically regarded as most important, the temperature decrease causes membrane productivity to decrease and further increase membrane selectivity. This is an inherent problem for pervaporation. It is very difficult to supply sufficient heat at the correct location (face of the membrane) to maintain constant temperature. As a result, productivity decreases exponentially and module count becomes unacceptably large. Further, the large temperature drop of the feed to the membrane due to the pressure drop often condenses the feed.

At least one prior art patent has identified that temperature has an effect on membrane performance. U.S. Pat. No. 5,679,133 discloses a glassy polymer membrane that is operated at temperatures of less than about 5° C. for separation of gas components. The patent claims, in an embodiment, a permeation method comprising contacting a first side of a gas separation membrane comprising a discriminating layer or region of a glassy polymer, wherein for the polymer cellulose triacetate is excluded, with the gas mixture while maintaining a difference in chemical potential from the first side of the membrane to a second side of the membrane, such that at least one first component gas of the gas mixture selectively permeates relative to at least one second component gas in the gas mixture from the first side of the membrane through the membrane to the second side of the membrane, the contacting occurring at a temperature of −5° C. or lower, wherein the membrane having a glassy region is selected so that, when using a mixture of 80 mole percent nitrogen and 20 mole percent oxygen as a feed at 30° C. with a pressure of 30 psia on the first side of the membrane and a vacuum of less than 1 mm Hg on the second side of the membrane, the permeability of oxygen in barriers is less than 2000. This patent illustrated that temperatures below ambient could be utilized in permeation procedures.

US Patent Application 2004/0000513A1 discloses a plurality of membrane modules disposed in a first product group, a second product group, and optionally one or more intermediate groups used for simultaneous recovery of a very pure permeate product and a desired non-permeate product from a mixture containing organic compounds. Examples of propylene/propane separation are given as simulated by a computer model. The preferred embodiment is a system of three membranes with propylene selectivity over propane. The embodiments disclosed pump feed stock (about 70% propylene/30% propane) in liquid form to a vaporizer and then to a first membrane. The permeate flows through, is compressed, cooled to 200° C. and passed through a second membrane. The permeate is collected as a stream comprising greater than 95% propylene. The non-permeate from the first membrane is passed to a third membrane. Permeate from the third membrane is compressed and passed back through the second membrane. Non-permeate from the third membrane is collected as a propane product.

U.S. Pat. No. 6,986,802 discloses a membrane device comprising multiple perm-selective membranes that are capable of effecting separation of a mixture of two or more compounds in a feed stock which when subjected to appropriately altered conditions of temperature and/or pressure exhibit a bubble point. The enthalpy of the feed stock is adjusted by a heat exchanger. Membrane Efficiency Index of the non-permeate fluid, when withdrawn, is within a range from about 0.5 to about 1.5. The Membrane Efficiency Index is defined as a ratio of the difference between the specific enthalpy of the feed stream entering the membrane device and specific enthalpy of the non-permeate fluid effluent to the difference between the specific enthalpy of the feed stream and the bubble point specific enthalpy of the non-permeate fluid at the non-permeate product pressure and composition. At an MEI of one, the non-permeate is disclosed as being a liquid at its bubblepoint.

U.S. Pat. No. 7,070,694 discloses an apparatus comprising a fractional distillation column and one or more membrane devices utilizing solid perm-selective membranes. The processes are stated as capable of use in simultaneous recovery of a very pure permeate product, a desired non-permeate stream, and one or more distillate products from a fluid mixture containing at least two compounds of different boiling point temperatures. The patent discloses the cooling effect produced by a membrane when a low pressure permeate is produced from a high pressure feed stock This is due to the Joule-Thompson effect. The patent further expresses the need for the incorporation heat integrated membrane apparatuses with pressure driven membrane separations.

However, these various prior art approaches require excessive capital costs and a multitude of membrane modules. Accordingly, there is a need in the art field for an improved membrane and/or membrane system for the separation of propylene and propane that uses fewer membrane modules and requires less capital cost.

SUMMARY OF THE INVENTION

The present invention provides a method of separating nonideal organic streams. For the purposes of the patent, nonideality is defined by the inability of the ideal gas law to describe the PVT (pressure volume temperature) behavior of the gas. Non ideality for organic gases increases with molecular weight:methane is more ideal than ethane, ethane is more ideal than propane, propane is more ideal than butane, and/or the like. Membrane based separation of nonideal organic gases leads to a temperature decrease on separation. The temperature change increases with increasing non-ideality of the stream. The temperature change arises due to reduction in pressure of the permeated gas from feed pressure to permeate pressure. This temperature change can be approximated by a Joule-Thompson expansion $(dT/dP)H$. The present invention provides a means to minimize the temperature drop on separation for gases. This method is particularly useful in the separation of organics, wherein the permeation process causes a significant temperature drop. This invention is particularly applicable to separation of organic streams, more particularly propylene and propane, wherein many negative aspects of membrane-based separation of propylene and propane are eliminated.

The current systems and methods allow membrane-based separation of propylene and propane, without a large change in temperature within or at a surface the membrane separator, thereby allowing a permeate stream and residue stream to be withdrawn at or about the temperature of the feed stream. The near isothermal operation greatly simplifies design, and operation of the system.

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated, in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE INVENTION

The following definitions and explanations are meant and intended to be controlling in any future construction unless clearly and unambiguously modified in the following Description or when application of the meaning renders any construction meaningless or essentially meaningless. In cases where the construction of the term would render it meaningless or essentially meaningless, the definition should be taken from Webster's Dictionary, $3^{rd}$ Edition. Definitions and/or interpretations should not be incorporated from other patent applications, patents, or publications, related or not, unless specifically stated in this specification or if the incorporation is necessary for maintaining validity.

Exemplary, non-limiting embodiments and/or disclosures of propane/propylene separation membranes that can be used with various embodiments of the present invention are disclosed in U.S. Pat. No. 4,374,657; U.S. Pat. No. 4,444,571; U.S. Pat. No. 4,857,078; U.S. Pat. No. 4,952,751; U.S. Pat. Nos. 4,978,430; 5,057,641; U.S. Pat. No. 5,273,572; U.S. Pat. No. 5,326,385; U.S. Pat. No. 5,679,133; U.S. Pat. No. 6,187,196; U.S. Pat. No. 6,187,987; U.S. Pat. No. 6,517,611; U.S. Pat. No. 6,986,802; U.S. Pat. No. 6,693,018; U.S. Pat. No. 7,025,804; and, U.S. Pat. No. 7,070,694, the contents of which are hereby incorporated by reference, as if they were presented herein in their entirety. In general, any membrane apparatus for use in the separation of propylene and propane is capable of use with the various embodiments of the present invention with varying degrees of performance, as would be readily apparent to one of ordinary skill in the art.

As used herein, a "fluid" is a continuous, amorphous substance whose molecules move freely past one another and that has the tendency to assume the shape of its container, for example, a liquid or a gas.

As used herein, "membrane apparatus" means and refers to flat sheet membranes, spiral wound flat sheet membranes, tubesheets, tubular tube membranes, hollow fiber membranes, and/or other membranes commonly used in industry.

As used herein, "RGP" means and refers to refinery grade propylene. Refinery grade propylene is nominally 70% propylene with propane as the other major component. RGP propylene composition varies widely. For the purposes of this invention RGP can range from 50% to 90%

As used herein, "CGP" means and refers to Chemical Grade Propylene. Chemical grade propylene is nominally 93% propylene with propane as the other major component. The propylene content of CGP can be higher than 93% but is typically less than 99% propylene.

Various embodiments of the present invention have wide applicability across the art field for systems and methods for the separation of propylene and propane. This disclosure will discuss application of the improvements of the present invention as it relates to primarily to a membrane-based system for the separation of propylene and propane wherein the feed fluid is capable of being a liquid and the produced product streams are capable of being liquid.

Other than in the operating examples, or where otherwise indicated, all numbers expressing quantities of components used herein are to be understood as modified in all instances by the term "about".

In general, various embodiments of a system of the present invention comprise at least a first membrane apparatus, a pump, and an evaporator, to produce a CGP product and a propane product from a feed stream comprising propylene and propane, such as, but not limited to a RGP feed stock. More specifically, in an embodiment of the present invention, a liquid feed comprising propylene and propane is introduced into an embodiment of a system of the present invention and a purified propylene product and a propane enriched product is extracted.

In the present invention, many of the negative aspects of membrane-based separation of a nonideal fluid stream are eliminated. In various embodiments of this process the feed is initially pumped or compressed to a relatively high pressure. A factor for selection of a pressure for the feed is such that the Joule Thompson coefficient is minimized.

The pressurized feed stream is then vaporized. Vaporization of the stream after pressurization reduces the heat required for vaporization relative to the vaporization prior to pressurization. This is due to the fact that the heat of vaporization decreases with increasing pressure. Pressurization of the feed has additional benefits. Higher pressure reduces total membrane count (i.e., the number of membranes required). Higher pressure increases the pressure-ratio (i.e., feed pressure to the membrane divided by permeate pressure from the membrane). Higher pressure ratio improves separation performance, in various embodiments.

In various embodiments of this process, the non-permeate portion of the feed stream may condense or at least partially condense on separation. As the non-permeate portion condenses, it evolves heat. This is commonly referred to as the heat of condensation. The evolution of heat at least partially offsets the temperature reduction created by the permeation process to keep the temperature of the membrane separator essentially constant. Through optimization of the feed pressure, the separation can be performed essentially athermally, i.e., remain at an essentially constant temperature. However, various embodiments of the present invention do allow for some temperature change, such that the separation is not essentially athermal.

Figure 2:
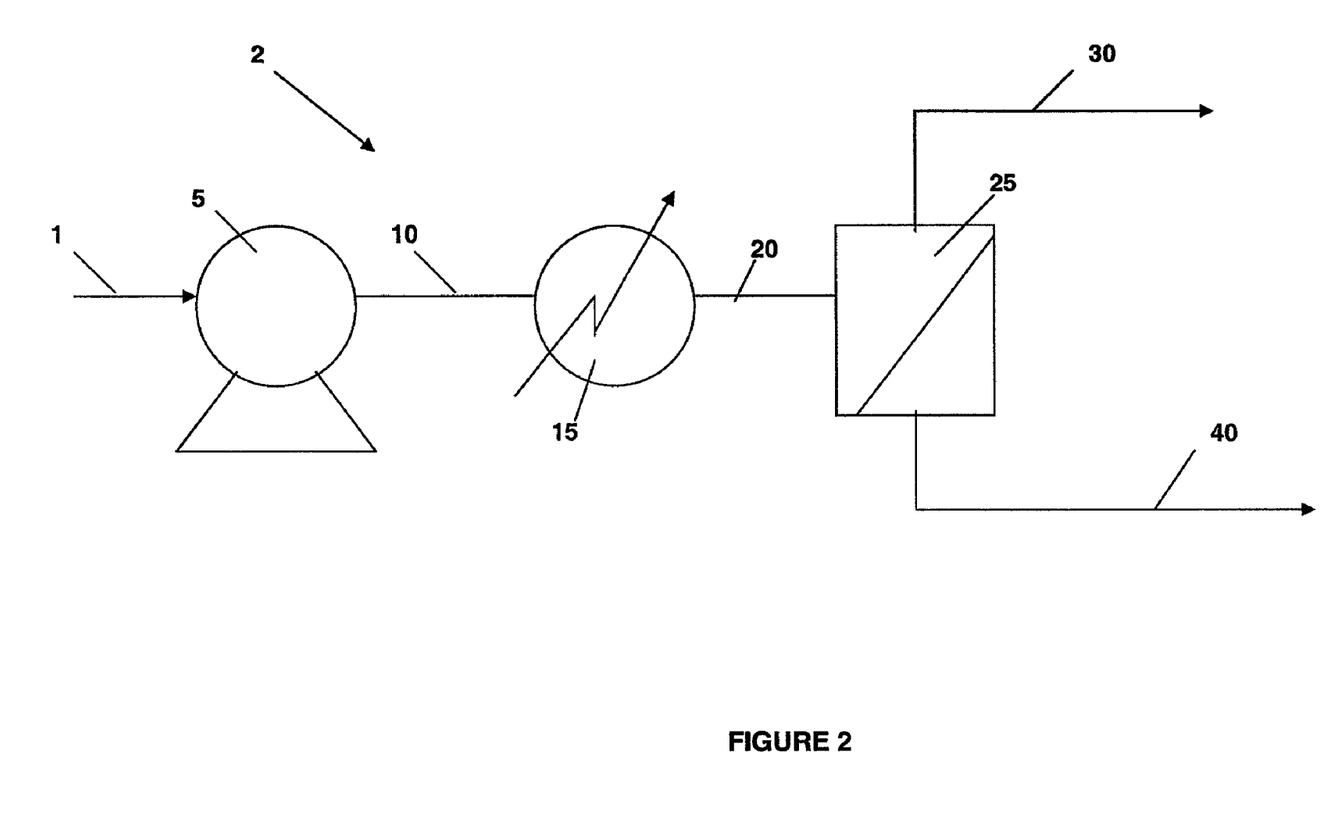
FIG. 2 is an illustration of an embodiment of a flow diagram showing an embodiment of the current system and/or method using a generally athermal membrane separation approach applied to a propylene/propane separation.

Now referring to FIG. 2, an illustration of an embodiment of a system of the present invention for the separation of propylene and propane is disclosed. System 2 comprises various elements, such as, but not limited to, pump 5, heat exchanger 15, and first membrane 25. These elements are interconnected by any means for connection common in the art, such as, but not limited to line(s), piping, valves, and/or the like. For example, in FIG. 3, a line introduces feed fluid 1 to pump 5, a line conveys the pressurized feed fluid 10 to heat exchanger 15, a line conveys the at least partially gaseous feed 20 to first membrane 25. From first membrane 25, a line conveys propylene enriched stream 30 and/or a line conveys propane enriched stream 40.

In an embodiment of operation of system 2, a feed stock or feed stream comprising at least propylene and propane is introduced or injected into system 2. In an embodiment, the feed stream is a refinery grade propylene (RGP) comprising about 70% propylene. However, RGP comprising other concentrations of propylene is possible and acceptable. In general, any feed stock comprising any concentration propane and propylene can be used in various embodiments of the present invention.

As disclosed, feed stream 1 is pumped to pressure in pump 5. In various embodiments, the pressure of feed stream 1 is pumped to about 300 psia to about 700 psia prior to introduction to membrane 25. In an embodiment, the pressure of feed stream 1 is pumped to about 300 psia to about 600 psia prior to introduction to membrane 25. In an alternate embodiment, the pressure of feed stream 1 is pumped to about 400 psia to about 500 psia prior to introduction to membrane 25. Further embodiments of a feed stream 1 are gas or at least partially gas and the pressure is raised by compression.

Membrane 25 is selective for propylene over propane. In general, any membrane capable of effecting a propylene/propane separation can be used. In various embodiments, membranes capable of operating in a condensing hydrocarbon environment and effecting a propylene/propane separation are preferred. An example of a membrane capable of operating in a hydrocarbon condensing environment is a polyimide membrane, and particularly a polyimide membrane made of polymers sold under the tradenames P84 or P84HT from HP Polymers GmbH. Preferred membranes of P84 or P84HT are disclosed in U.S. Pat. No. 7,018,445, titled POLYIMIDE BLENDS FOR GAS SEPARATION MEMBRANES, and U.S. patent application titled IMPROVED SEPARATION MEMBRANE BY CONTROLLED ANNEALING OF POLYIMIDE POLYMERS, filed on Mar. 2, 2005. The entire disclosures of these applications are incorporated herein by this reference.

In general, the selectivity of the propylene/propane membrane for propylene should be at least about 3.0 to about 20.0. In an embodiment, the selectivity for propylene is about 6.0 to about 15.0. In an alternate embodiment, the selectivity for propylene is about 8.0 to about 13.0. In yet an alternate embodiment, the selectivity for propylene is about 10.0 to about 12.0.

In an alternate embodiment, the selectivity of the propylene/propane membrane should be greater than at least about 2.5 for propylene. In an alternate embodiment, the selectivity for propylene is greater than about 6.0. In an alternate embodiment, the selectivity for propylene is greater than about 8.0. In yet an alternate embodiment, the selectivity for propylene is greater than about 10.0.

Non-permeate stream 30 will exit membrane 25 at about the temperature at which stream 20 entered membrane 25. However, due to the cooling effect of membrane 25, stream 40 can be expected, in various embodiments, to be cooler than stream 20. Either or both of stream 30 and/or stream 40 may be further processed as is desired. Further embodiments will disclose various further processing.

In an embodiment, the permeate stream, propylene enriched, will pass from membrane 25 and be collected as a product. In an embodiment, purity of the stream 30 is about at least 93% propylene. However, in various embodiments, the purity can vary as designed. In an embodiment, the propylene product extracted is used as a CGP product. In various alternate embodiments, a gas product is capable of being collected.

In various embodiments, the percentage recovery of propylene is from about 50% to about 99%. In an alternate embodiment, the percentage recovery of propylene is from about 75% to about 99%. In an alternate embodiment, the percentage recovery of propylene is from about 85% to about 99%.

In various embodiments, the percentage recovery of propane is from about 75% to about 99. In an alternate embodiment, the percentage recovery of propane is from about 80% to about 92%.

Figure 3:
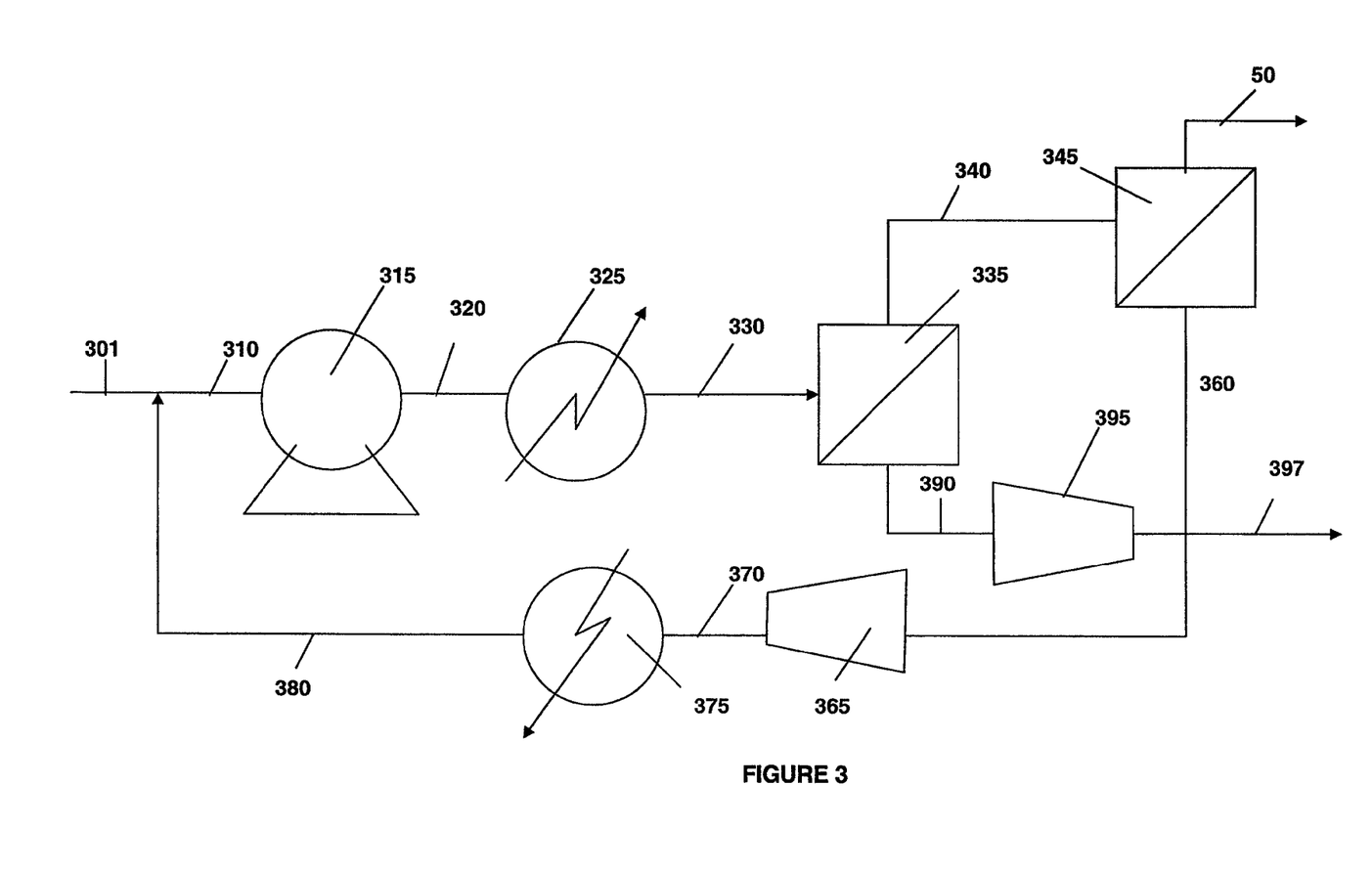
FIG. 3 is an illustration of an alternate embodiment of a flow diagram showing an embodiment of the current system and/or method.

Now referring to FIG. 3, an illustration of an alternate embodiment of a system of the present invention for the separation of propylene and propane is disclosed. System 300 comprises various elements, such as, but not limited to, pump 315, heat exchanger 325, first membrane 335, second membrane 345, first compressor 395, second compressor 365, first evaporator 325, and first condenser 375.

These elements are interconnected by any means for connection common in the art, such as, but not limited to line(s), piping, valves, and/or the like. For example, in FIG. 4, a line introduces feed fluid 301 to pump 315, a line conveys the pressurized feed fluid 320 to first heat exchanger 325, a line conveys the at least partially gaseous feed 330 to first membrane 335. From first membrane 335, a line conveys non-permeate stream 340 and/or a line conveys propylene enriched stream 390.

Stream 390 is conveyed to first compressor 395 and conveyed as a high pressure propylene stream 397. Stream 397 can be collected as a product, sent for further processing, used elsewhere in the process, and/or the like.

Stream 340 is typically depleted in propylene as compared to stream 330. However, a large component of stream is capable of being propylene. In an embodiment, stream 340 is conveyed to a second membrane 345. Second membrane 345 is selective for propylene over propane, such that a propane-enriched stream 350 is extracted and a propylene-enriched stream 360 is extracted.

In general, the selectivity of the propylene/propane membrane for propylene should be at least about 3.0 to about 20.0. In an embodiment, the selectivity of propylene over propane is about 6.0 to about 15.0. In an alternate embodiment, the selectivity of propylene over propane is about 8.0 to about 13.0. In yet an alternate embodiment, the selectivity of propylene over propane is about 10.0 to about 12.0.

In an alternate embodiment, the selectivity of the propylene/propane membrane should be greater than at least about 3.0. In an alternate embodiment, the selectivity of propylene over propane is greater than about 6.0. In an alternate embodiment, the selectivity of propylene over propane is greater than about 8.0. In yet an alternate embodiment, the selectivity of propylene over propane is greater than about 10.0.

Non-permeate stream 340 will exit membrane 335 at about the temperature at which stream 330 entered membrane 335. However, due to the cooling effect of membrane 335, stream 350 can be expected, in various embodiments, to be cooler than stream 330.

The permeate stream 360, propylene enriched, will pass from membrane 345 and into second compressor 365. High pressure stream 370 is then conveyed to condenser 375, wherein a liquid propylene-enriched stream is capable of being injected into stream 1, forming a combined stream 310.

Figure 4:
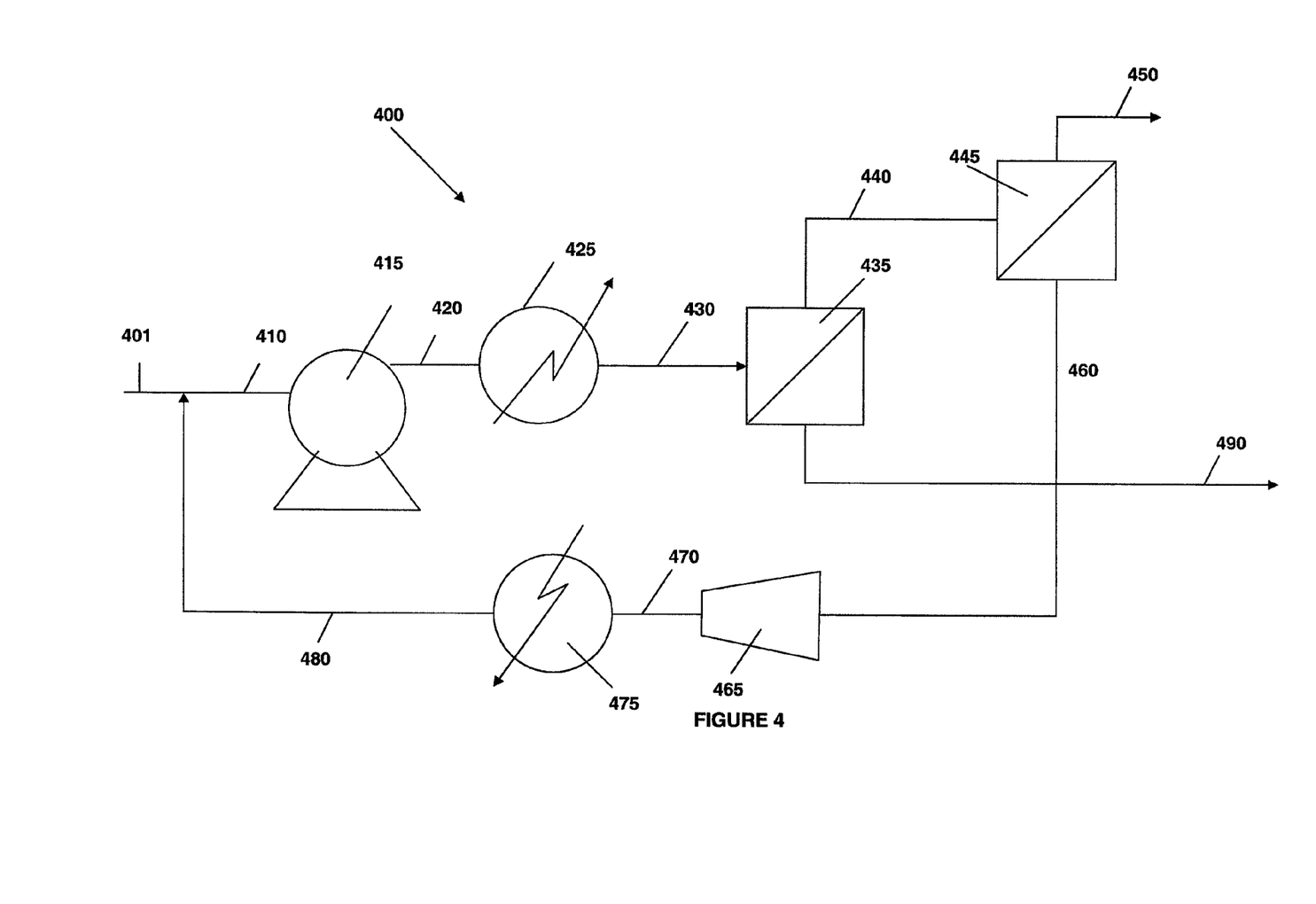
FIG. 4 is an illustration of an alternate embodiment of a flow diagram showing an embodiment of the current system and/or method.

Now referring to FIG. 4, an illustration of an alternate embodiment of a system of the present invention for the separation of propylene and propane is disclosed. System 400 comprises various elements, such as, but not limited to, pump 415, first heat exchanger 425, first membrane 435, second membrane 445, first compressor 465, and first condenser 475.

First membrane 435 and second membrane 445 are capable of being constructed/formed to be selective for a variety of components. In an embodiment, membrane 435 and membrane 445 are selective for propylene over propane.

Figure 5:
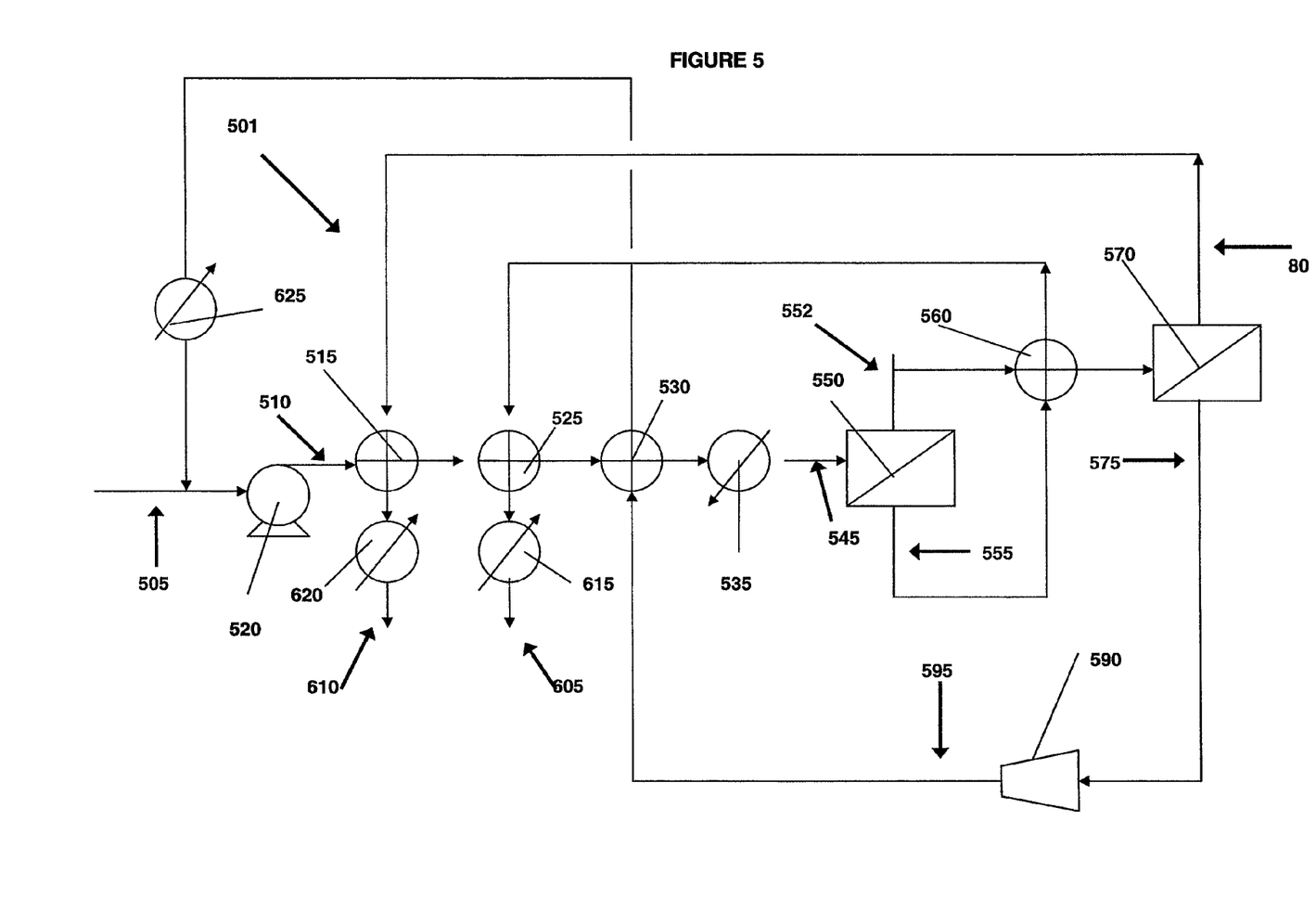
FIG. 5 is an illustration of an alternate embodiment of a flow diagram showing an embodiment of the current system and/or method.

Now referring to FIG. 5, an illustration of an alternate embodiment of a system of the present invention for the separation of propylene and propane is disclosed. System 501 discloses a feed stream 505, pump 520, first heat exchanger 515, second heat exchanger 525, third heat exchanger 530, evaporator 535, first membrane 550, heat exchanger 560, second membrane 570, compressor 590, first condenser 615, second condenser 620, and third condenser 625.

Stream 505 is typically introduced to system 501 as a liquid and pumped to pressure in pump 520, producing some heat. Stream 510 is passed through various heat exchangers for cooling and/or heating. In an embodiment, stream 510 is cooled against streams 580, 550, and/or 595. However, in various embodiments, one or more of streams 580, 550, and/or 595 act to heat stream 510.

Evaporator 535 evaporates stream 510 into at least partially gaseous stream 545. Stream 545 is conveyed to first membrane 550. The non-permeate stream 520 is passed across a heat exchanger 560 with permeate stream 550. Heat exchanger acts to heat stream 550 and cool stream 520. However, little cooling of stream 520 will be realized considering the volume of stream 520 being greater than that of stream 550. Stream 520 can then be collected as a liquid propylene product stream 605 after passing through condenser 615.

In an embodiment, there is no cooling of stream 520 in heat exchanger 560. In an alternate embodiment, there is minimal cooling of stream 520 in exchanger 550. In an alternate embodiment, stream 520 is cooled by more than a minimal amount.

Stream 520 is then conveyed to second membrane 570 wherein a further propylene-depleted stream 580 is removed and a further propylene-enriched stream 575 is removed. Stream 580 will be at least partially gaseous and therefore act to heat stream 510 in exchanger 515. Stream 580 is capable also of being condensed in condenser 620 and collected as a propane/propylene liquid product.

Stream 575 will be pressure depleted and propylene-enriched. In an embodiment, for process enhancement, at least a portion of stream 575 is compressed as stream 595, condensed in condenser 625 and reintroduced into system 501 into stream 501.

Further embodiments further comprise additional membranes as desired. For example, a further membrane may be added to further separate propylene from stream 575, such as to produce a Polymer Grade Propylene Product (PGP) product. Further, a different arrangement of heat exchangers, evaporators, compressors, and condensers can be used within the general inventive guidelines of the present invention. The addition of another membrane allows improving propylene purity without the necessity of improving or modifying membrane structure, i.e., membrane selectivity and/or the like. In an embodiment, adding at least one additional membrane increases the purity of propylene to at 99%.

Further embodiments of the preset invention contemplate a process for the separation of propylene and propane. In an embodiment, the feed stream is a propylene/propane stream at a temperature T1. The pressure P1 of the liquid propylene/propane stream is increased to a pressure P1 of about 400 to 600 psia. The liquid stream is then vaporized and heated to temperature sufficient to establish process conditions of P2 and T2 at the membrane separator inlet or feed port that is just above or at the dewpoint. The propylene/propane stream enters the membrane separator and partially or fully condenses in the membrane separator as the propylene permeates through the membrane and the remaining stream (primarily propane) is removed as a non-permeate liquid or two-phase stream gas/liquid stream. The propylene permeate is compressed and condensed as required to form a propylene liquid product. The non-permeate stream is then passed through another membrane separator wherein the non-permeate is collected as a propane product and the permeate propylene-rich stream is recycled back to the feed stream.

Accordingly, in an embodiment, a process of the present invention generally comprises the steps of feeding a feed stream comprising propylene and propane to a first membrane at a temperature at or slightly above the dewpoint of propylene, said membrane having a selectivity for propylene of at least 5.0, whereby at least a portion of a first non-permeate stream condenses on or about the first membrane; extracting a permeate propylene enriched stream, wherein the permeate stream is extracted at or about the same temperature as the feed stream; condensing the permeate stream; and, recovering the permeate stream as a propylene product stream.

EXAMPLES

It has been discovered that higher pressure reduces the module count and the higher pressure-ratio (feed pressure to the membrane divided by permeate pressure from the membrane) improves separation performance. Further, the evolution of heat by the condensation of the process feed fluid helps to keep the temperature constant and reduce capital cost and operational cost of the system.

It has been found that traditional gas separation systems require 95% more membranes, 12% more horsepower and 9.5% more energy for processing RGP than embodiments of the current inventive process. The current inventive process uses ⅓ more pump horsepower than the traditional gas separation approach.

Figure 6:
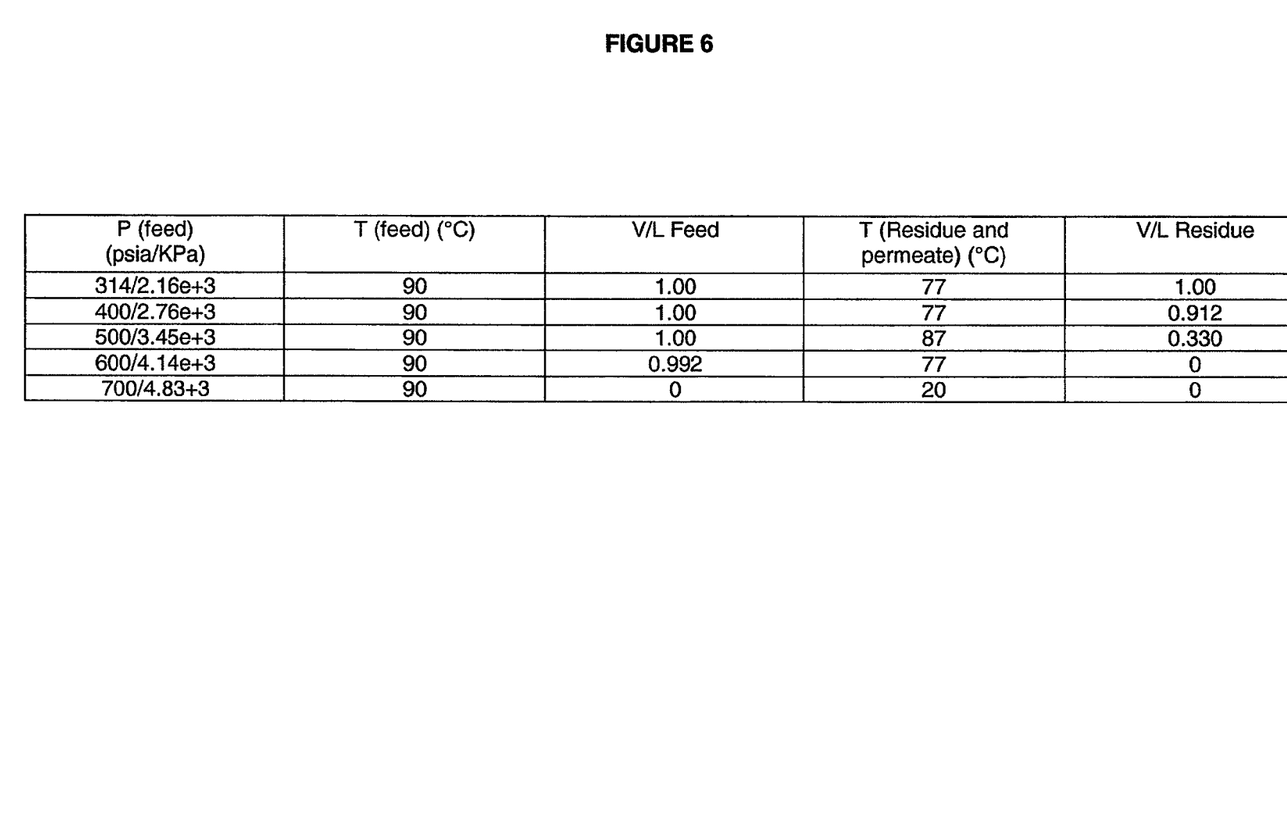
FIG. 6 is a Table illustrating Condensation and Temperature Change at various operating pressures in Propylene Separation.

Reference to FIG. 6 illustrates the effect of varying pressure of a feed gas in the embodiment of a propylene separation membrane, Refinery Grade Propylene (RGP), at a temperature of 90° C. on the temperature of the permeate gas and the associated vapor/liquid (V/L) proportion of the permeate gas. The results indicate that feed pressures between about 400 psia and about 500 psia (2.76e+3 kPa to 3.45e+3 kPa) produce a substantial liquid permeate without a significant drop in temperature.

Application of these concepts is illustrated in the following examples. For each of these examples, a membrane with a selectivity of propylene to propane of 11 is assumed.

Example 1

A simulation was performed based upon the system illustrated in FIG. 2. The intent of this system is the recovery of higher purity propylene. The system incorporates a membrane (25) with a propylene to propane selectivity of 11.3 MMscfd. Now referring to FIG. 2, an example of a system of the present invention for the separation of propylene and propane is disclosed. A feed of 3 MMscfd at 200 psia and 30 C is introduced to System 2. Pump 5 pressurizes the stream 500 psia. Evaporator (15) vaporizes the feed reaching an ultimate temperature of 90° C. Membrane (25) with an inherent propylene to propane selectivity of 11 is used to separate the feed into a propylene enriched product (40) and a propane enriched product (30). The propylene product is recovered at 93% propylene purity at 40 psia. Propylene recovery is 70%. The propane purity is 57% and propane recovery is 88%. The pump for this system requires 44 kw and the evaporator (heat exchanger) requires 662 kW. Table 1 lists the various properties of the streams for Example 1.

TABLE 1

Stream Properties for Example 1

| | Stream # | | | | |
|---|---|---|---|---|---|
| | 1 | 10 | 20 | 30 | 40 |
| T (° C.) | 30 | 33 | 95 | 77 | 77 |
| P (psia) | 200 | 500 | 500 | 40 | 499 |
| V/L | 0 | 0 | 1 | 1 | 0.8 |
| Flow (MMscfd) | 3 | 3 | 3 | 1.6 | 1.4 |
| % propylene | 70 | 70 | 70 | 93.1 | 43 |
| % propane | 30 | 30 | 30 | 6.9 | 57 |

Example 2

A simulation was also performed based upon the system illustrated in FIG. 3. The system is capable of high recovery of increased purity propylene and high recovery of increased purity propane. A feed of 3 MMscfd at 200 psia and 30 C is introduced to the system outline in FIG. 2. Pump (315) pressurizes the stream 500 psia. Evaporator (heat exchanger) (325) vaporizes the feed reaching an ultimate temperature of 90° C. Membrane (335) separates the feed into a propylene enriched product at 40 psia (390). The propylene product is compressed to system feed pressure by Compressor (395). The non-permeate stream (340) is reheated to 90 C and further processed by membrane (335) into a 95% propane product (50) and a low pressure propylene-enriched stream. Stream 360 is compressed by compressor (364) and subsequently condensed by condenser (375). The resulting stream is comingled with the feed (301). The combined stream is fed to the membrane system.

A system based on FIG. 3 is capable of producing 93% propylene at 98% recovery and a 95% propane product at 83% recovery. Energy requirements for the system are as follows.

Pump (315): 13.8 kW

Evaporator (heat exchanger) (325): 921 kW

Condenser (375): 344 kW

Compressor (365): 96 kW

Compressor (395): 175 kW

Table 2 lists the various properties of the streams for Example 2.

Compared with Example 1 the current system increases propylene recovery and produces a high purity propane stream.

TABLE 2

Stream Properties for Example 2

| | Stream # | | | | | | | |
|---|---|---|---|---|---|---|---|---|
| | 301 | 320 | 330 | 390 | 340 | 341 | 350 | 360 |
| T (° C.) | 30 | 33 | 90 | 80 | 80 | 90 | 35 | 35 |
| P (psia) | 200 | 500 | 500 | 40 | 499 | 499 | 499 | 30 |
| V/L | 0 | 0 | 1 | 1 | 0.8 | 1 | 0.5 | 1 |

TABLE 2-continued

Stream Properties for Example 2

| | Stream # | | | | | | |
|---|---|---|---|---|---|---|---|
| | 301 | 320 | 330 | 390 | 340 | 341 | 350 | 360 |
| Flow (MMscfd) | 3 | 4.17 | 4.17 | 2.22 | 1.95 | 1.95 | 0.79 | 1.16 |
| % propylene | 70 | 69.8 | 69.8 | 93.1 | 43 | 43 | 4.9 | 69.7 |
| % propane | 30 | 30.2 | 30.2 | 6.9 | 57 | 57 | 95.1 | 30.3 |

Example 3

A simulation was also performed based upon the system illustrated in FIG. 4. The system is capable of high recovery of increased purity propylene and high recovery of increased purity propane and elimination of the propylene product compressor. A feed of 3 MMscfd at 200 psia and 30 C is introduced to the system outline in FIG. 3. Pump (415) pressurizes the stream 500 psia. Evaporator (325) vaporizes the feed reaching an ultimate temperature of 90° C. Membrane (435) separates the feed into a propylene enriched product at 200 psia (490). No compression is required to achieve system feed pressure. The non-permeate stream (340) is reheated to 90 C and further processed by membrane (435) into a 95% propane product (50) and a low pressure propylene-enriched stream. Stream 460 is compressed by compressor (465) and subsequently condensed by condenser (475). The resulting stream is comingled with the feed (301). The combined stream is fed to the membrane system.

A system based on FIG. 3 is capable of producing 93% propylene at 98% recovery and a 95% propane product at 83% recovery. Energy requirements for the system are as follows.
  Pump (315): 18 kW
  Evaporator (heat exchanger) (325): 1210 kW
  Condenser (375): 737 kW
  Compressor (365): 203 kW Example 3 demonstrates identical performance to Example 2 without the necessity of propylene product compression.

TABLE 4

Stream Properties for Example 3

| | Stream # | | | | | | |
|---|---|---|---|---|---|---|---|
| | 401 | 420 | 430 | 490 | 440 | 441 | 450 | 460 |
| T (° C.) | 30 | 32 | 90 | 82 | 82 | 90 | 35 | 35 |
| P (psia) | 200 | 500 | 500 | 40 | 499 | 499 | 499 | 30 |
| V/L | 0 | 0 | 1 | 1 | 0.8 | 1 | 0.5 | 1 |
| Flow (MMscfd) | 3 | 5.49 | 5.49 | 2.2 | 3.27 | 3.27 | 0.78 | 2.49 |
| % propylene | 70 | 76.29 | 76.29 | 93.1 | 63.7 | 63.7 | 4.9 | 82.1 |
| % propane | 30 | 23.71 | 23.71 | 6.9 | 36.3 | 36.3 | 95.1 | 17.8 |

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

What is claimed is:

1. A process for the membrane-based separation of propane and propylene, said process comprising the steps of:
   feeding a feed stream comprising propylene and propane to a first membrane at a temperature at or slightly above the dewpoint of propylene and a pressure between about 400 psia and about 600 psia, said first membrane having a selectivity for propylene of at least 6.5, whereby at least a portion of a first non-permeate stream condenses on said first membrane; and
   extracting a first permeate propylene enriched stream, wherein said permeate stream is extracted at or about the same temperature as said feed stream.

2. The process of claim 1, further comprising the step of condensing said first permeate stream.

3. The process of claim 1, further comprising the step of extracting a non-permeate product from said first membrane as a propane product stream.

4. The process of claim 1, wherein propylene of greater than about 93% purity is recovered.

5. The process of claim 1, further comprising the steps of:
   feeding said non-permeate stream to a second membrane at a temperature at or slightly above the dewpoint of propylene and a pressure between about 400 psia and about 600 psia, said second membrane having a selectivity for propylene of at least 2.5, whereby at least a portion of a second non-permeate stream condenses on said second membrane;
   extracting a second permeate propylene enriched stream, wherein said permeate stream is extracted at or about the same temperature as the feed stream; and
   combining said second permeate propylene enriched stream with said feed stream.

6. The process of claim 5, wherein propane of at least about 95% purity is recovered.

7. The process of claim 6, wherein the propane product stream is collected as a liquid or as a two-phase gas/liquid stream having a propane purity of at least about 95%.

8. The process of claim 1, wherein said feed stream comprises about 70% propylene.

9. A process for the membrane-based separation of propane and propylene, said process comprising the steps of:
feeding a feed stream comprising propylene and propane to a first membrane at a temperature at or slightly above the dewpoint of propylene,
said first membrane having a selectivity for propylene of at least 5.0;
extracting a first permeate propylene enriched stream, wherein said permeate stream is extracted at or about the same temperature as said feed stream;
condensing said first permeate stream; and,
recovering said first permeate stream as a propylene product stream.

10. The process of claim 9, further comprising the step of extracting a non-permeate product from said first membrane as a propane product stream.

11. The process of claim 9, wherein propylene of at least 93% purity is recovered.

12. The process of claim 9, further comprising feeding said non-permeate stream to a second membrane at a temperature at or slightly above the dewpoint of propylene, said second membrane having a selectivity for propylene of at least 5.0;
extracting a second permeate propylene enriched stream, wherein said permeate stream is extracted at or about the same temperature as the feed stream; and,
combining said permeate stream with said feed stream.

13. The process of claim 10, wherein propane of least 95% purity is recovered.

14. The process of claim 11, wherein the propane product stream is collected as a liquid or as a two-phase gas/liquid stream at a purity of at least about 95%.

15. The process of claim 9, wherein said feed stream comprises about 70% propylene.

* * * * *